United States Patent
Nishimura

(10) Patent No.: US 7,972,333 B2
(45) Date of Patent: Jul. 5, 2011

(54) HIGH FREQUENCY INCISION TOOL FOR ENDOSCOPE

(75) Inventor: Miyuki Nishimura, Nagano (JP)

(73) Assignee: River Seiko Medical Limited Company, Okaya-shi, Nagano (JP)

(*) Notice: Subject to any disclaimer, the term of this patent is extended or adjusted under 35 U.S.C. 154(b) by 954 days.

(21) Appl. No.: 11/436,511

(22) Filed: May 19, 2006

(65) Prior Publication Data

US 2006/0264930 A1    Nov. 23, 2006

(30) Foreign Application Priority Data

May 20, 2005    (JP) ................................ P2005-176933

(51) Int. Cl.
*A61B 18/14*    (2006.01)
(52) U.S. Cl. ................. 606/48; 606/50; 606/51; 606/52
(58) Field of Classification Search .............. 606/45–46, 606/51–52, 205–207
See application file for complete search history.

(56) References Cited

U.S. PATENT DOCUMENTS

| | | | |
|---|---|---|---|
| 5,540,685 A * | 7/1996 | Parins et al. | 606/51 |
| 5,810,805 A * | 9/1998 | Sutcu et al. | 606/45 |
| 6,019,758 A * | 2/2000 | Slater | 606/51 |
| 6,443,970 B1 * | 9/2002 | Schulze et al. | 606/171 |
| 6,953,430 B2 * | 10/2005 | Kidooka | 600/104 |
| 7,052,492 B2 * | 5/2006 | Swanson et al. | 606/32 |
| 7,182,775 B2 * | 2/2007 | de Guillebon et al. | 606/207 |
| 7,306,599 B2 * | 12/2007 | Karasawa et al. | 606/51 |
| 2001/0041893 A1 | 11/2001 | Bartel | |
| 2003/0191465 A1 * | 10/2003 | Yahagi et al. | 606/48 |
| 2005/0010211 A1 | 1/2005 | Suzuki | |

FOREIGN PATENT DOCUMENTS

| | | |
|---|---|---|
| DE | 103 54 275 A1 | 7/2004 |
| JP | 58-136105 | 9/1983 |
| JP | 2002-95671 | 4/2002 |
| JP | 2003-299667 | 10/2003 |
| JP | 2004-350938 | 12/2004 |

* cited by examiner

*Primary Examiner* — Roy D Gibson
*Assistant Examiner* — Amanda Scott
(74) *Attorney, Agent, or Firm* — Drinker Biddle & Reath LLP

(57) ABSTRACT

A high-frequency incision tool for endoscope comprises a sheath inserted through and extracted from a treatment tool guide lumen of an endoscope; an operation unit connected to the rear of the sheath; a pair of electrode blades disposed in parallel and oriented forward at the front position of the sheath, the pair of electrode blades opening forward and closing back through remote manipulation of the operation unit; and a planar portion provided at the tip of at least one of the electrode blades, the planar portion having a projected area, when viewed from the front, larger than the cross sectional areas of the electrode blades at a portion close to their front ends.

16 Claims, 17 Drawing Sheets

CROSS SECTION A-A

CROSS SECTION B-B

CROSS SECTION C-C

HIGH FREQUENCY INCISION TOOL FOR ENDOSCOPE

BACKGROUND OF THE INVENTION

The present invention relates to a high frequency incision tool for endoscope for use through a treatment tool guide lumen of an endoscope.

High frequency incision tools for endoscope are available in various shapes depending on applications. As an example used for separation of mucous membranes, JP-A-2003-299667 discloses an incision tool including scissors-like electrodes in which a pair of electrode blades disposed in parallel and oriented forward at the front position of a sheath can be remotely opened and closed from the rear end of the sheath.

However, the above-mentioned related high frequency incision tool for endoscope has a problem that at the beginning of use, when the front end of the incision tool protrudes from the treatment tool guide lumen of the endoscope into the body, the tip of the thin electrode blade may violently press and damage the surface the mucous membrane, or even puncture the mucous membrane at worst. Although the use of cup-like electrode blades of bawl-shaped biopsy forceps eliminates such a problem, such a cup of the bawl-like electrode blade blocks the direct endoscopic view of part of the portion to be incised during high-frequency incision, compromising patient safety.

Furthermore, in a separation procedure of a mucous membrane from the underlying muscle layer, the incision is carried out while the electrode blades are inserted between the superficial mucous membrane and the muscle layer and a high-frequency current is applied. However, with the related high-frequency incision tool for endoscope, the electrode blades may touch a portion that is not intended to be incised, resulting in possible burning of the mucous membrane and muscle layer. Moreover, before applying the high-frequency current, it is required to create a gap between the superficial mucous membrane and the muscle layer in a mechanical manner. Although thin electrode blades may be used for that purpose, it may only be pushed in the mucous membrane but cannot create a gap between the mucous membrane and the muscle layer as desired.

SUMMARY OF THE INVENTION

The invention has been made to solve such problems and aims to provide a high frequency incision tool for endoscope in which the front end of the incision tool can be protruded from a treatment tool guide lumen of an endoscope into the body in a safe manner without damaging the surface of a mucous membrane, and in a separation procedure of the mucous membrane, a gap can be created between the mucous membrane and the muscle layer in a mechanical and reliable manner, allowing high-frequency incision to be carried out only on the portion that is intended to be incised in a safe manner.

In order to solve the problem, the present invention is characterized by having the following arrangements.

(1) A high-frequency incision tool for endoscope comprising:
 a sheath inserted through and extracted from a treatment tool guide lumen of an endoscope;
 an operation unit connected to a rear of the sheath;
 a pair of electrode blades disposed in parallel and oriented forward at a front position of the sheath, the pair of electrode blades being adapted to open and close through remote manipulation of the operation unit; and
 a planar portion provided at a tip of at least one of the electrode blades, the planar portion having a projected area, when viewed from the front, larger than across sectional areas of the electrode blades at a portion close to front ends thereof.

(2) The high-frequency incision tool according to (1), wherein the planar portion is formed so as to project sideways from the tip portion of the electrode blade.

(3) The high-frequency incision tool according to (2), wherein the tip of the electrode blade is formed so as to bend sideways to form an L-shape.

(4) The high-frequency incision tool according to (2), wherein each of the pair of electrode blades deviates sideways from extension of a center axis line of the front end portion of the sheath.

(5) The high-frequency incision tool according to (2), wherein the tip of the electrode blade is formed in a T-shape with a crossbar of the T projecting sideways in opposite directions.

(6) The high-frequency incision tool according to (1), wherein at least a surface of the planar portion is electrically insulated from the electrode blades.

(7) The high-frequency incision tool according to (6), wherein the planar portion is formed of an electrically insulating member attached to the tip of the electrode blade.

(8) The high-frequency incision tool according to (7), wherein the electrically insulating member encloses at least the tip of the electrode blade and the vicinity of the tip thereof.

(9) The high-frequency incision tool according to (6), wherein the planar portion is formed of an electrically insulating member attached to an outer surface of the electrode blade.

(10) The high-frequency incision tool according to (9), wherein the electrically insulating member is an adhesive adhered to an area extending from the tip to a back side of the electrode blade, the back side representing a side viewed in the open/close direction of the blades.

(11) The high-frequency incision tool according to (6), wherein the electrically insulating members are attached to the electrode blade so that the electrode blade is sandwiched between the electrically insulating members that connect to each other through a hole drilled through the electrode blade to form an integral part.

(12) The high-frequency incision tool according to (6), wherein saw teeth having successive projections and recesses are formed on opposite sides of the pair of electrode blades, and an apex of the saw tooth projects toward the closing direction beyond the electrically insulating member attached to the electrode blade.

(13) The high-frequency incision tool according to (1), wherein the pair of the electrode blades is opened and closed around a shaft disposed in the front end portion of the sheath and an operation wire for driving the pair of the electrode blades is inserted through the sheath.

(14) The high-frequency incision tool according to (1), wherein the pair of electrode blades is biased in the opening direction and opened and closed by advancing and retracting the electrode blades out of or into the front end of the sheath with an operation wire inserted through the sheath.

(15) The high-frequency incision tool according to (13), wherein the operation wire is formed of a conductive member through which a high-frequency current is applied to the electrode blades.

(16) The high-frequency incision tool according to (1) wherein each of the pair of the electrode blades is formed into a shape in which a cup of bawl-shaped biopsy forceps is cut in half.

(17) The high-frequency incision tool according to (1), wherein a casing tube fits around the sheath throughout its length and the sheath and the electrode blades can freely rotate around an axis of the casing tube relative to the casing tube.

(18) The high-frequency incision tool according to (17), wherein the operation unit can rotate the sheath and the electrode blades relative to the casing tube.

(19) The high-frequency incision tool according to (1), wherein the sheath is formed of a close-wound metal coil and the casing tube is formed of an electrically insulating tube.

(20) A high-frequency incision tool for endoscope comprising:
    a sheath inserted through and extracted from a treatment tool guide lumen of an endoscope;
    an operation unit connected to a rear of the sheath;
    a pair of electrode blades disposed in parallel and oriented forward at a front position of the sheath, the pair of electrode blades being adapted to open and close through remote manipulation of the operation unit; and
    an electrically insulating member attached to tips of the electrode blades.

(21) The high-frequency incision tool according to (20), wherein the electrically insulating member encloses at least the tip of the electrode blade and the vicinity of the tip thereof.

(22) The high-frequency incision tool according to claim (20), wherein the electrically insulating member is an adhesive adhered to an area extending from the tip to a back side of the electrode blade, the back side representing a side viewed in the open/close direction of the blades.

(23) The high-frequency incision tool according to (20), wherein the electrically insulating members are attached to the electrode blade so that the electrode blade is sandwiched between the electrically insulating members that connect to each other through a hole drilled through the electrode blade to form an integral part.

(24) The high-frequency incision tool according to (20), wherein saw teeth having successive projections and recesses are formed on opposite sides of the pair of electrode blades, and an apex of the saw tooth projects toward the closing direction beyond the electrically insulating member attached to the electrode blade.

According to the high frequency incision tool for endoscope of the invention, since the tip of at least one of the electrode blades is provided with a planar portion with a projected area, when viewed from the front, larger than the cross sectional area of the electrode blade at a portion close to its front end, the front end of the incision tool can be protruded from a treatment tool guide lumen of an endoscope into the body in a safe manner without damaging the surface of a mucous membrane, and in a separation procedure of the mucous membrane, a gap can be created between the mucous membrane and the muscle layer in a mechanical and reliable manner. Furthermore, since at least the surface of the planar portion is electrically insulated from the electrode blades, high-frequency incision can be carried out only on the portion that is intended to be incised in a safe manner.

Figure 1:
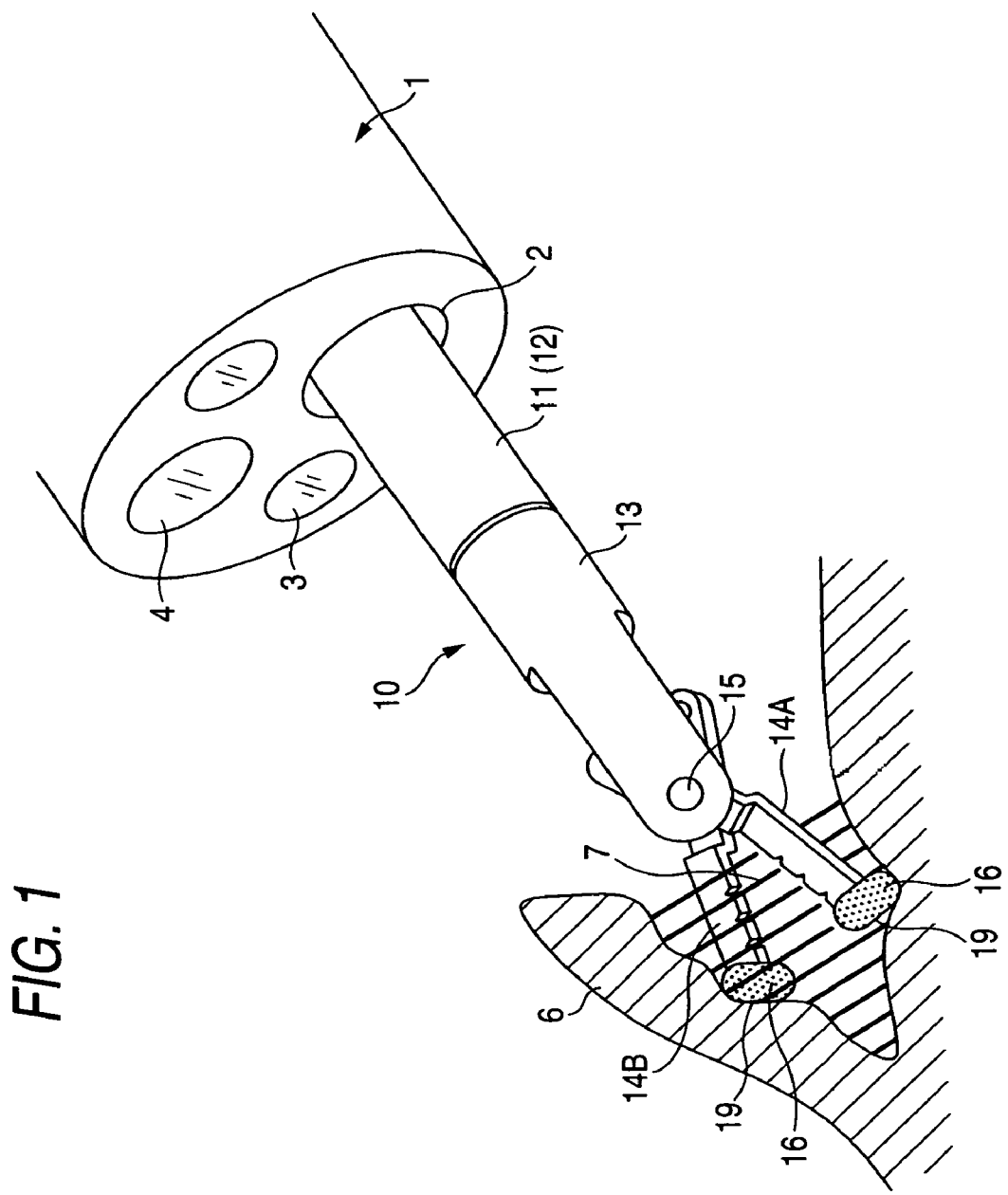
FIG. 1 is a perspective view of the high-frequency incision tool for endoscope according to the first embodiment of the invention in use.

1: endoscope
2: treatment tool guide lumen
10: high-frequency incision tool
11: sheath
12: casing tube
13, 130: front support member
14A, 14B: electrode blade
15: rotation support shaft
16; insulating coating (electrically insulating member)

17: operation wire
19: planar portion
116: adhesive (electrically insulating member)
141: saw-tooth
216: electrically insulating member

DETAILED DESCRIPTION OF PREFERRED EMBODIMENTS

First Embodiment

Embodiments of the invention will be specifically described hereinafter with reference to the drawings. FIG. 1 shows a state that a high-frequency incision tool 10 of the invention is inserted through a treatment tool guide lumen 2 of an endoscope 1 and a front end portion of the high-frequency incision tool 10 protrudes from the treatment tool guide lumen 2 into a body cavity of a patient. This process is illuminated by illumination light radiated from an illumination window 3 of the endoscope 1 and endoscopically observed through an observation window 4.

The portion of the high-frequency incision tool 10 that is inserted through and extracted from the treatment tool guide lumen 2 is constructed in such a manner that a flexible sheath 11 is coated with a casing tube 12 formed of a flexible, electrically insulating tube, through which an operation wire formed of a conductive stainless steel wire or the like is inserted. A front support member 13 is fixedly connected to the front end of the sheath 11, and a pair of electrode blades 14A and 14B formed of a conductive metal is supported by the front end thereof. The electrode blades 14A and 14B can be opened forward and closed back like a nipper or a pair of scissors by pivoting them around a rotation support shaft 15. An electrically insulating coating 16 is attached to the tip of each of the electrode blades 14A and 14B.

Figure 2:
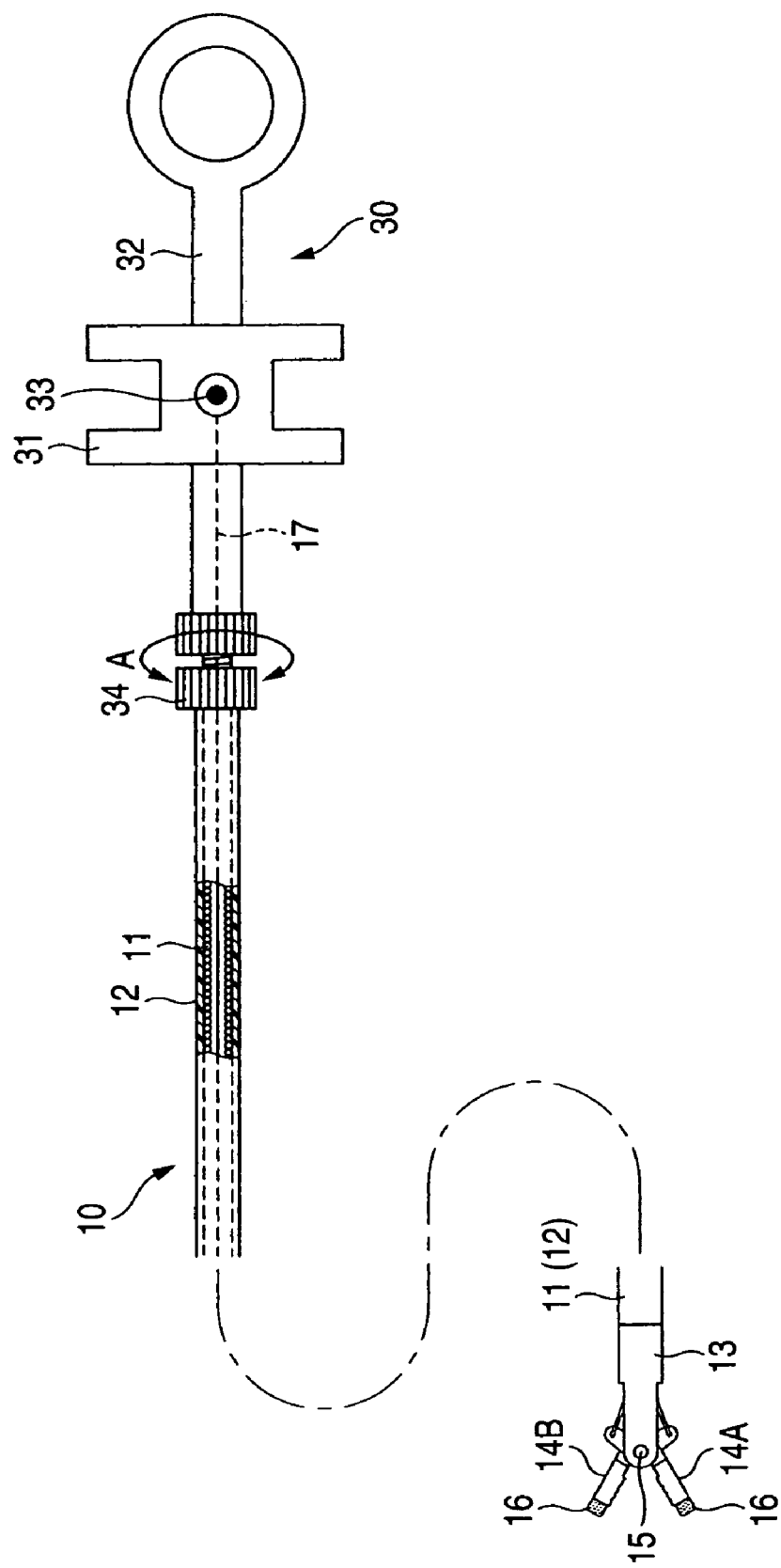
FIG. 2 is a side view illustrating the overall arrangement of the high-frequency incision tool for endoscope according to the first embodiment of the invention, part of which is shown in cross-section.

FIG. 2 shows the overall arrangement of the high-frequency incision tool 10. An operation unit 30 disposed at the proximal end of the sheath 11 is provided with an operation slider 31 fixedly connected to the rear end of an operation wire 17. The operation slider 31 freely slides along an operation unit body 32 connected to the rear end of the sheath 11. The operation slider 31 is also provided with a connection socket 33 for connecting a high-frequency power supply cable (not shown), through which a high-frequency current can be applied to the operation wire 17.

The casing tube 12 formed of a fluororesin tube or the like fits around the sheath 11 throughout its length and can freely and independently rotate around its axis. The casing tube 12 can be independently rotated around its axis relative to the other members by rotating a collet 34, which is attached to the rear end of the casing tube 12, relative to the operation unit body 32 in the direction indicated by the arrow A. Therefore, when the high-frequency incision tool 10 is inserted through the treatment tool guide lumen 2 of the endoscope 1, the sheath 11 and the electrode blades 14A and 14B provided at the front end portion thereof can be freely rotated around the axis by rotating the operation unit 30.

Figure 3:
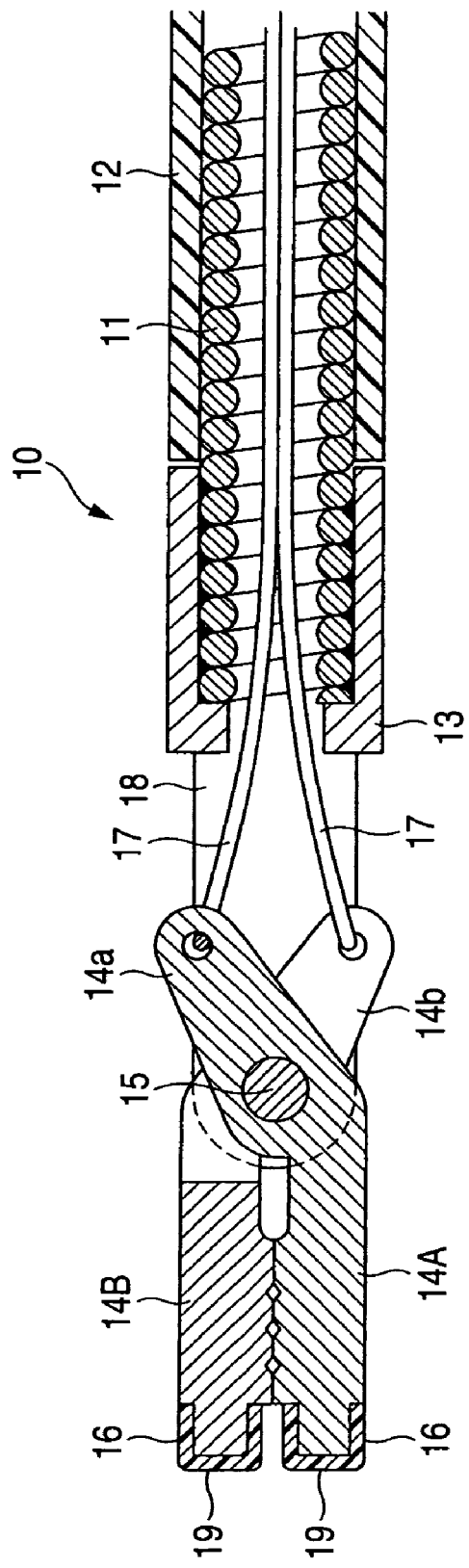
FIG. 3 is a cross-sectional side view of the high-frequency incision tool for endoscope according to the first embodiment of the invention when the electrode blades at the front end portion thereof are closed.
Figure 4:
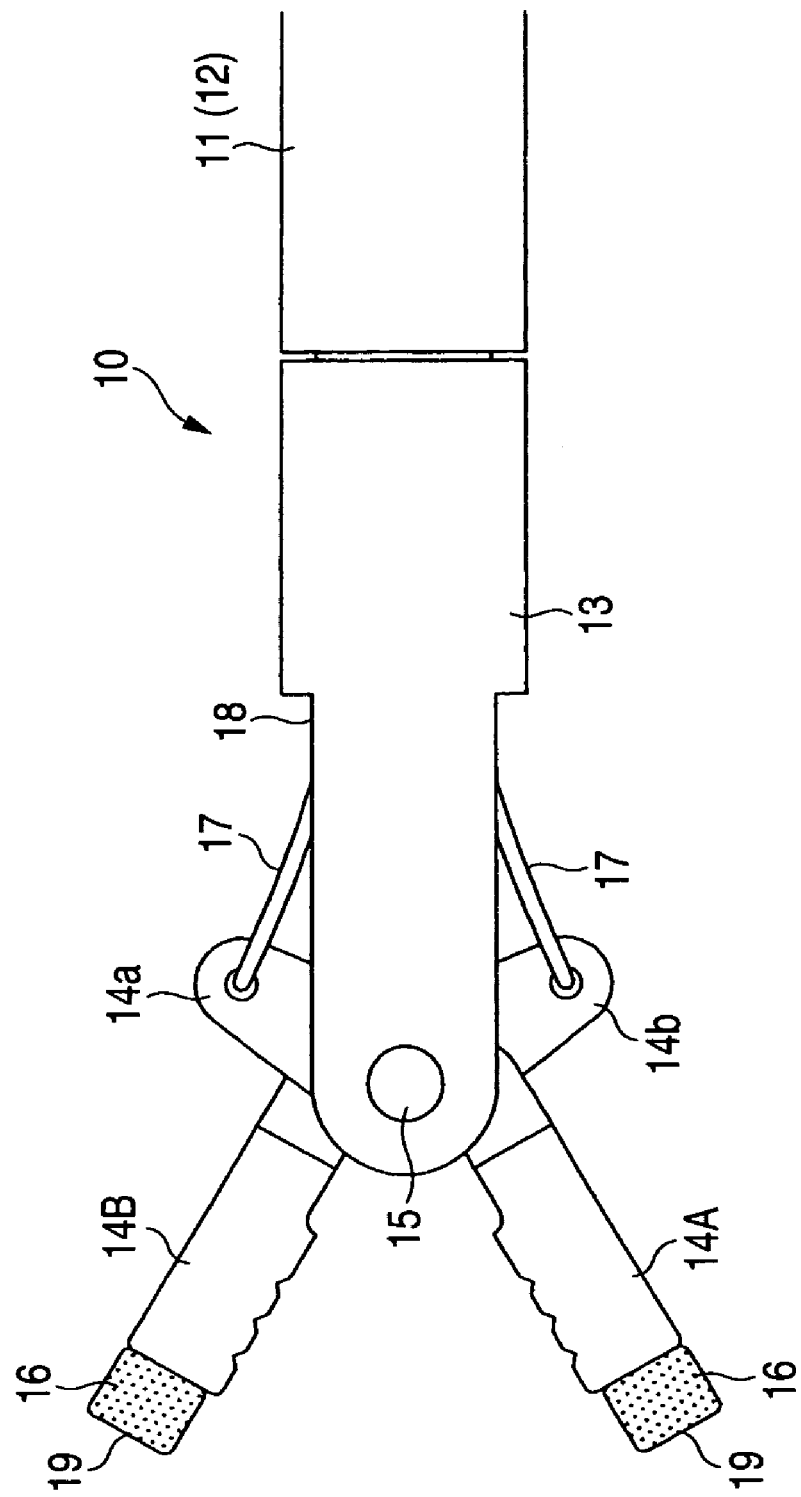
FIG. 4 is a side view of the high-frequency incision tool for endoscope according to the first embodiment of the invention when the electrode blades at the front end portion thereof are open.
Figure 5:
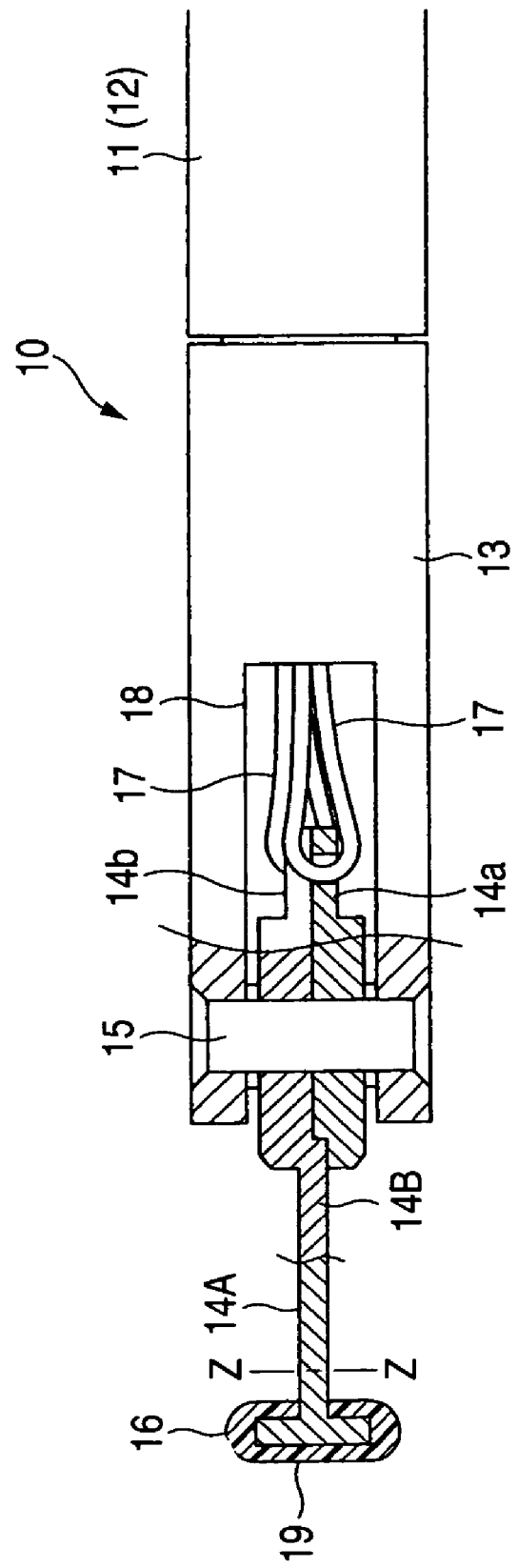
FIG. 5 is a partial cross-sectional plan view of the front end portion of the high-frequency incision tool for endoscope according to the first embodiment of the invention.

FIG. 3 is a side cross-sectional view when the electrode blades 14A and 14B at the front end portion of the high-frequency incision tool 10 are closed. FIG. 4 is a side view when the electrode blades 14A and 14B are open. FIG. 5 is a plan partial cross-sectional view. It should be noted that each cross-sectional view includes cross sections at different planes. The configuration of the front end portion of the high-frequency incision tool 10 according to this embodiment will be described below. The sheath 11 is formed of, for example, a close-wound stainless steel wire and is free to bend. Alternatively, the sheath 11 may be formed of a flexible tube or the like. The front support member 13 is formed of stainless steel, ceramic, highly heat-resistant plastic (such as PEEK) or the like and its front portion branches off with a slit 18 therebetween. The rotation support shaft 15 is fixed to the front support member 13 extending across the slit 18.

Each of the pair of electrode blades 14A and 14B is shaped into a generally thin plate. When closed, as shown in FIG. 3, they are oriented in parallel and straight forward in front of the rotation support shaft 15 such that the thin sides of the electrode blades 14A and 14B face and abut to each other. Recesses for better engagement with mucous membranes or blood vessels may or may not be formed on the abutting surfaces. Alternatively, the pair of electrode blades 14A and 14B may not abut to each other when closed, but pass through each other like the blades of a pair of scissors.

The portions of the electrode blades 14A and 14B that extend backward from the rotation support shaft 15 are accommodated in the slit 18 and form drive arms 14a and 14b for driving the electrode blades 14A and 14B. The tip of the operation wire 17 branches off into two, which engage the portions close to the rear ends of the drive arms 14a and 14b. Thus, when the operation wire 17 is pushed from the operation unit 30, the pair of the electrode blades 14A and 14B pivot around the rotation support shaft 15 into an open position where the two blades form a V-shape with the open end of the V pointing forward, as shown in FIG. 4. By pulling the operation wire 17 from the operation unit 30, the pair of electrode blades 14A and 14B is closed as shown in FIG. 3. A high-frequency current can be applied to the electrode blades 14A and 14B through the operation wire 17.

Each tip of the pair of electrode blades 14A and 14B is formed in a T-shape with the crossbar of the T projecting sideways in both right and left directions, as shown in FIG. 5. The projections are coated with electrically insulating coating 16 (electrically insulating member). The insulating coating 16 may be formed of, for example, highly heat-resistant plastic such as fluororesin, ceramic, or enamel materials. Consequently, the front end surface of the insulating coating 16 forms a planar portion with a projected area, when viewed from the front, larger than the cross sectional area of each of the electrode blades 14A and 14B at a portion close to its front end (approximately 3 to 10 times larger in this embodiment). The term "cross sectional area of each of the electrode blades 14A and 14B at a portion close to its front end" is not the cross-sectional area of the tip portion of each of the electrode blades 14A and 14B where the electrode blade bends sideways but the cross-sectional area at a portion where the electrode blades 14A and 14B face forward (cross section taken along the line Z-Z).

Therefore, even when the high-frequency incision tool 10 violently protrudes from the treatment tool guide lumen 2 of the endoscope 1 into the body cavity of the patient, the impact is applied to mucous membranes through the planar portion 19 which has a large projected area when viewed from the front without damage to the mucous membranes, allowing a safe insert operation of the high-frequency incision tool 10 without extra care. As shown in FIG. 1, when performing separation of mucous membrane or the like in which the mucous membrane 6 is separated from the underlying muscle layer, the first step is inserting the electrode blades 14A and 14B between the mucous membrane 6 and the muscle layer and opening the electrode blades. The block-like insulating coating 16 can reliably create a gap between the mucous membrane 6 and the muscle layer in a safe and mechanical manner. Then, a high-frequency treatment is performed in which a high-frequency current is applied to the electrode blades 14A and 14B in order to incise (or coagulate) muscles (or blood vessels) 7 between the mucous membrane 6 and the muscle layer. Since the insulating coatings 16 push aside the mucous membrane 6 and underlying muscle layer and hence the electrode blades 14A and 14B do not touch them, the muscles (or blood vessels) 7 can be incised (or coagulated) without burning the mucous membrane 6 or muscle layer. The portion to be incised by the electrode blades 14A and 14B can be directly viewed through the observation window 4 of the endoscope 1. In order to obtain better endoscopic observation, the electrode blades 14A and 14B can be repositioned as required by rotating the sheath 11 around the axis to change the orientation of the electrode blades 14A and 14B.

Second and Third Embodiment

Figure 6:
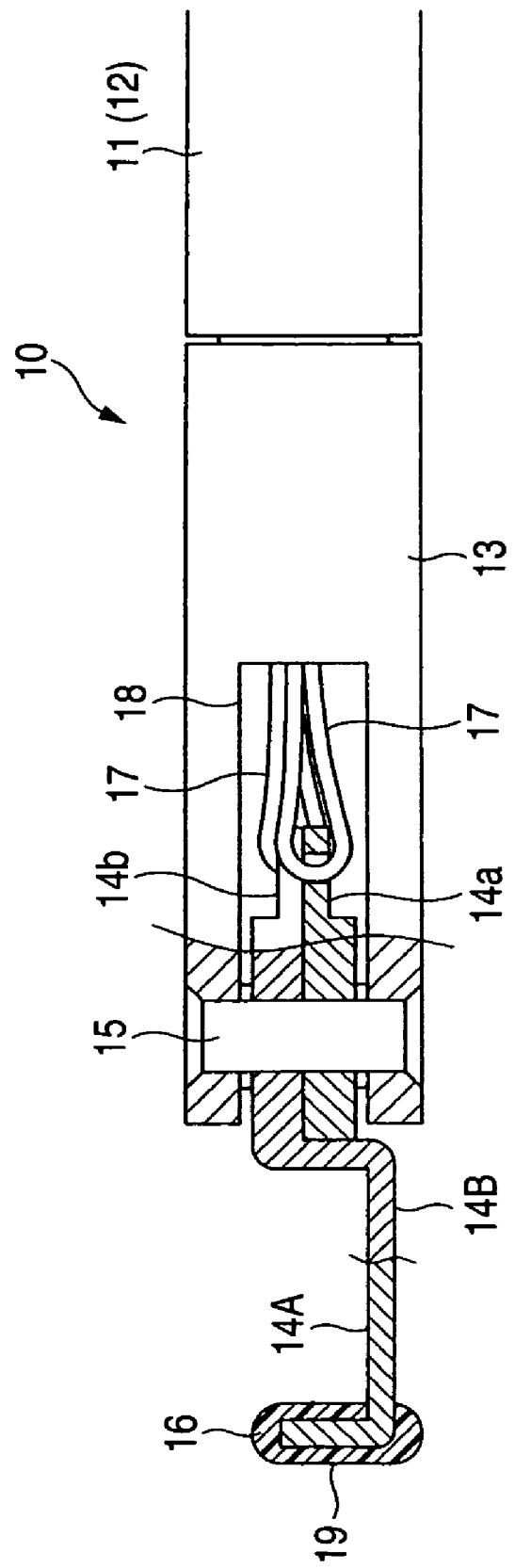
FIG. 6 is a partial cross-sectional plan view of the front end portion of the high-frequency incision tool for endoscope according to the second embodiment of the invention.
Figure 7:
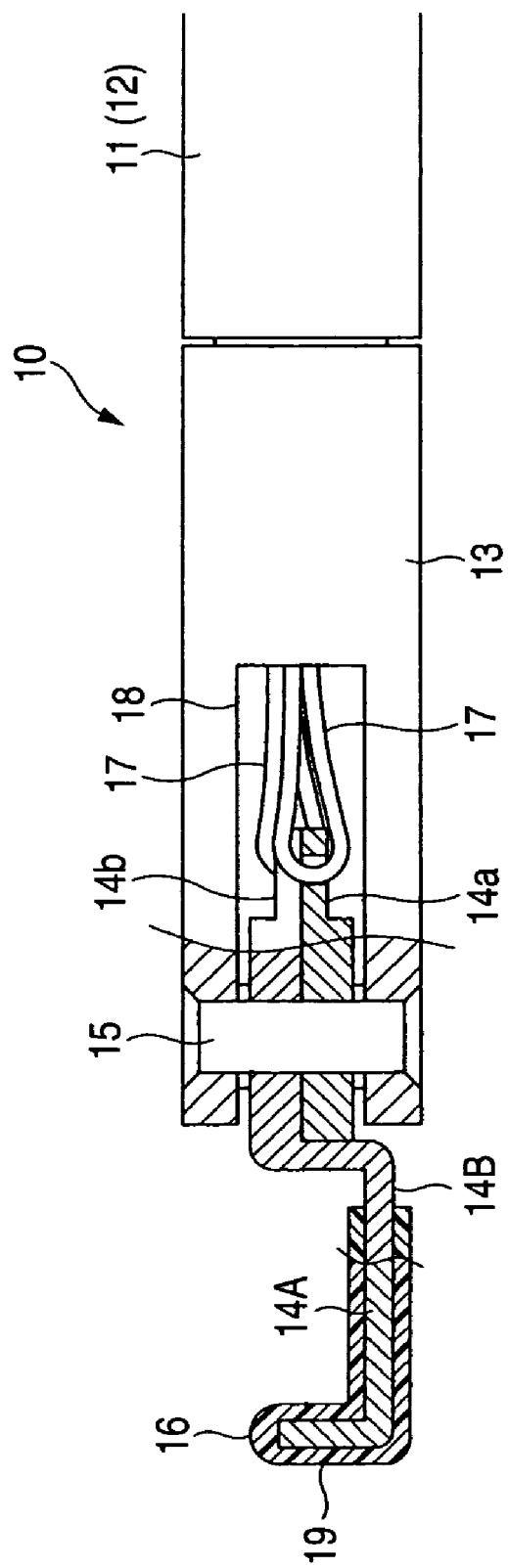
FIG. 7 is a partial cross-sectional plan view of the front end portion of the high-frequency incision tool for endoscope according to the third embodiment of the invention.

FIGS. 6 and 7 show the front end portion of the high-frequency incision tool 10 according to second and third embodiments of the invention. Each of the electrode blades 14A and 14B deviates sideways from the extension of the center axis line of the front end portion of the front support member 13 and each of the tip portions of the electrode blades 14A and 14B bends sideways (inward) to form an L-shape. Thus configured electrode blades 14A and 14B are easier to manufacture.

In the second embodiment shown in FIG. 6, the insulating coating 16 encloses the portion of each of the electrode blades 14A and 14B that is distal from the bent position. In the third embodiment shown in FIG. 7, the insulating coating 16 encloses not only the portion of each of the electrode blades 14A and 14B that is distal from the bent position but also the portion backward therefrom. As shown in the figures, the insulating coating 16 only needs to enclose the tip portion of each of the electrode blades 14A and 14B and therearound.

Fourth Embodiment

Figure 8:
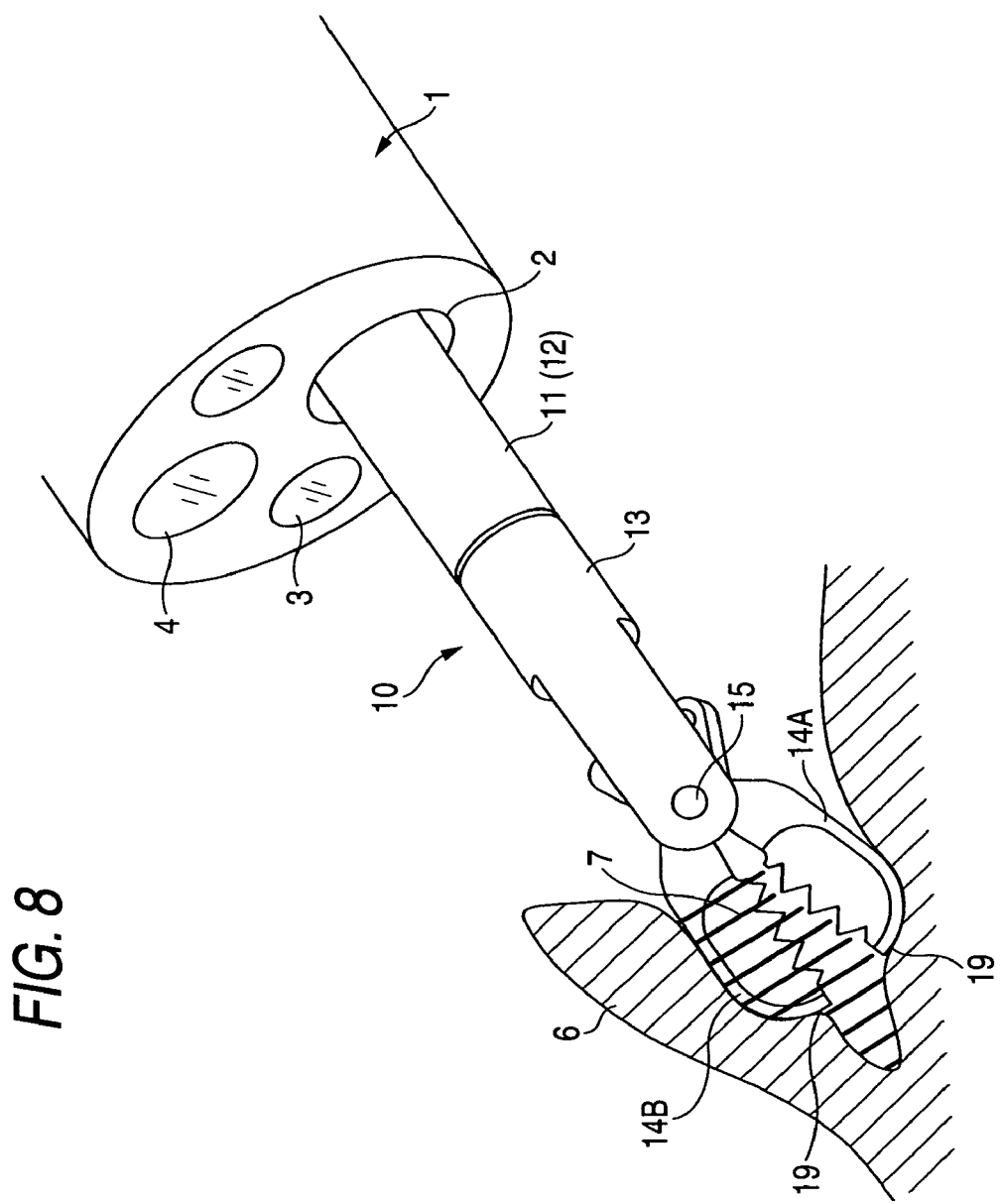
FIG. 8 is a perspective view of the high-frequency incision tool for endoscope according to the fourth embodiment of the invention in use.
Figure 9:
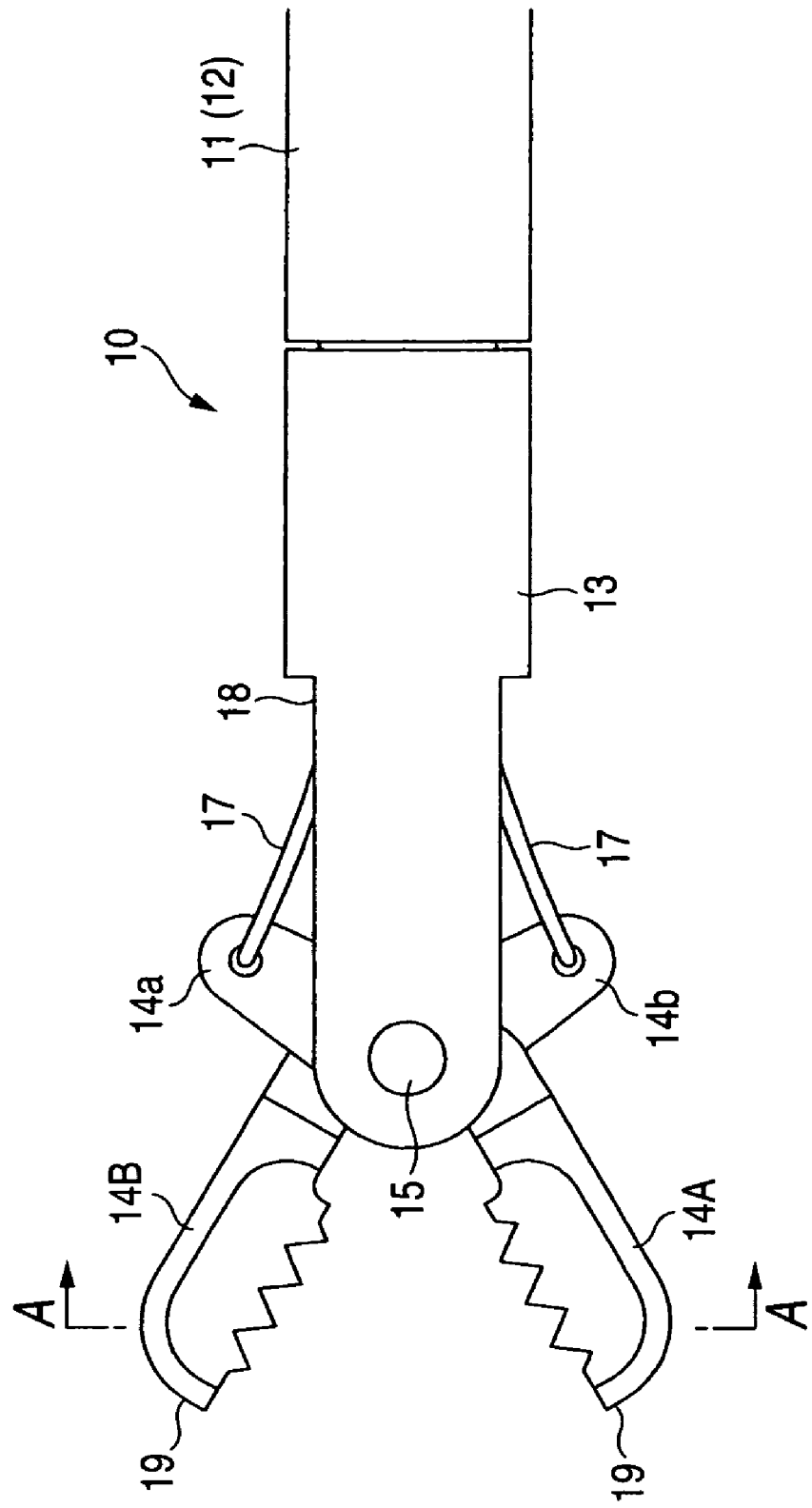
FIG. 9 is a side view of the high-frequency incision tool for endoscope according to the fourth embodiment of the invention when the electrode blades at the front end portion thereof are open.
Figure 10:
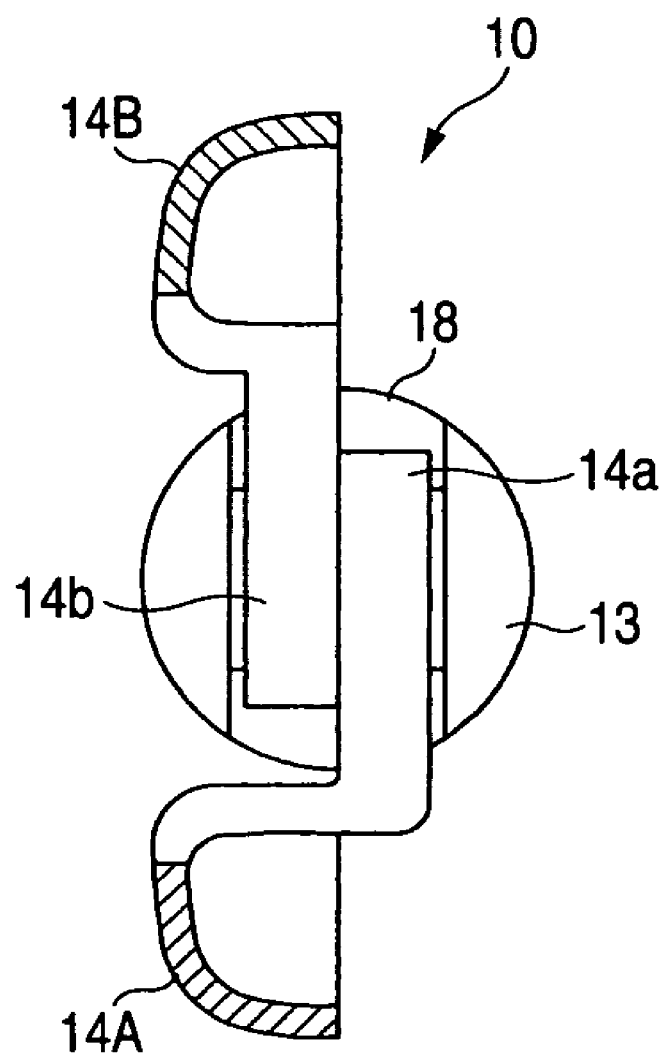
FIG. 10 is a cross-sectional view of the high-frequency incision tool for endoscope according to the fourth embodiment of the invention taken along the line A-A shown in FIG. 9.

FIG. 8 shows that the front end portion of the high-frequency incision tool 10 according to a fourth embodiment of the invention protrudes from the treatment tool guide lumen 2 of the endoscope 1 to perform high-frequency incision (or coagulation). The pair of the electrode blades 14A and 14B in this embodiment is formed such that a half side of a cup of known bawl-shaped metal biopsy forceps is cut and the half-cut bawls face to each other, as shown in FIG. 9, the side view, and FIG. 10, the cross-sectional view taken along the line A-A shown in FIG. 9.

In this configuration again, at the tip of each of the electrode blades 14A and 14B is formed a curved planar portion 19 that has a larger projected area, when viewed from the front, than the cross-sectional area of each of the electrode blades 14A and 14B at a portion close to its front end. This allows the electrode blades to be protruded into the body cavity without damaging the mucous membrane 6 and mechanically push open the mucous membrane 6 without damage. Since the incising part of each of the electrode blades 14A and 14B is formed of only the half-cut portion, high-frequency treatment can be performed while ensuring a direct view of the portion being incised through the observation window 4 of the endoscope 1. The outer surface of the bawl-like portion of each of the electrode blades 14A and 14B may be coated with electrically insulating coating or the like.

Fifth Embodiment

Figure 11:
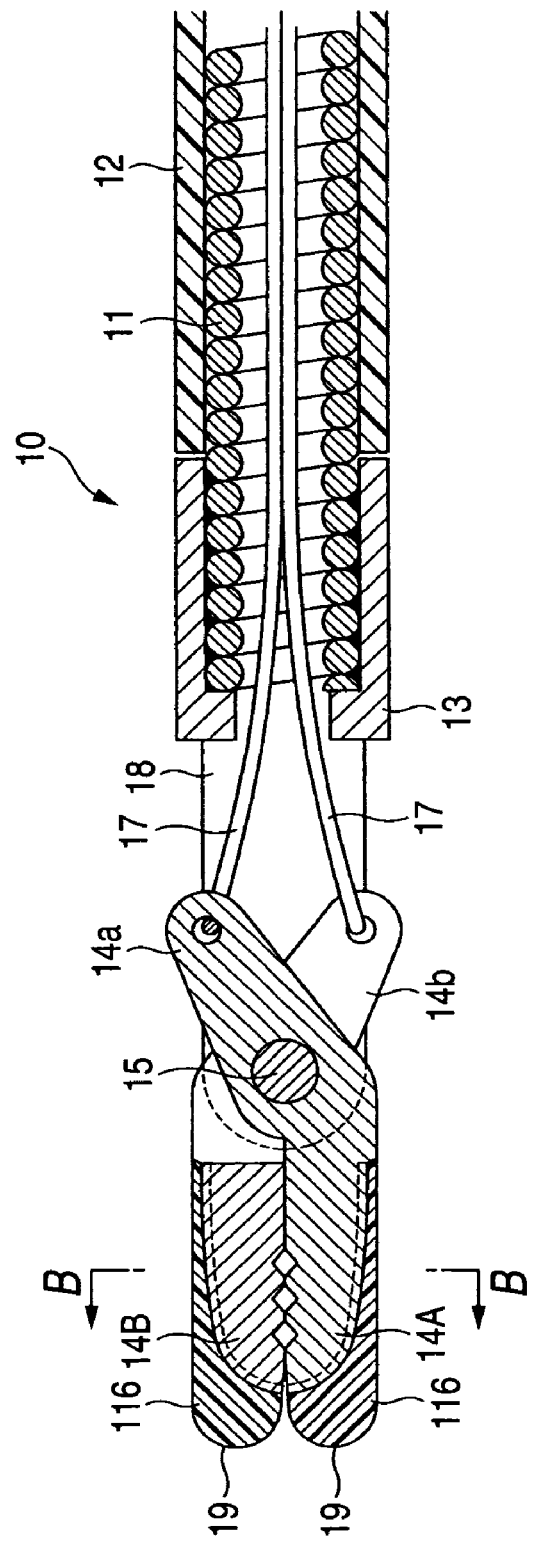
FIG. 11 is a cross-sectional side view of the high-frequency incision tool for endoscope according to the fifth embodiment of the invention when the electrode blades at the front end portion thereof are closed.
Figure 12:
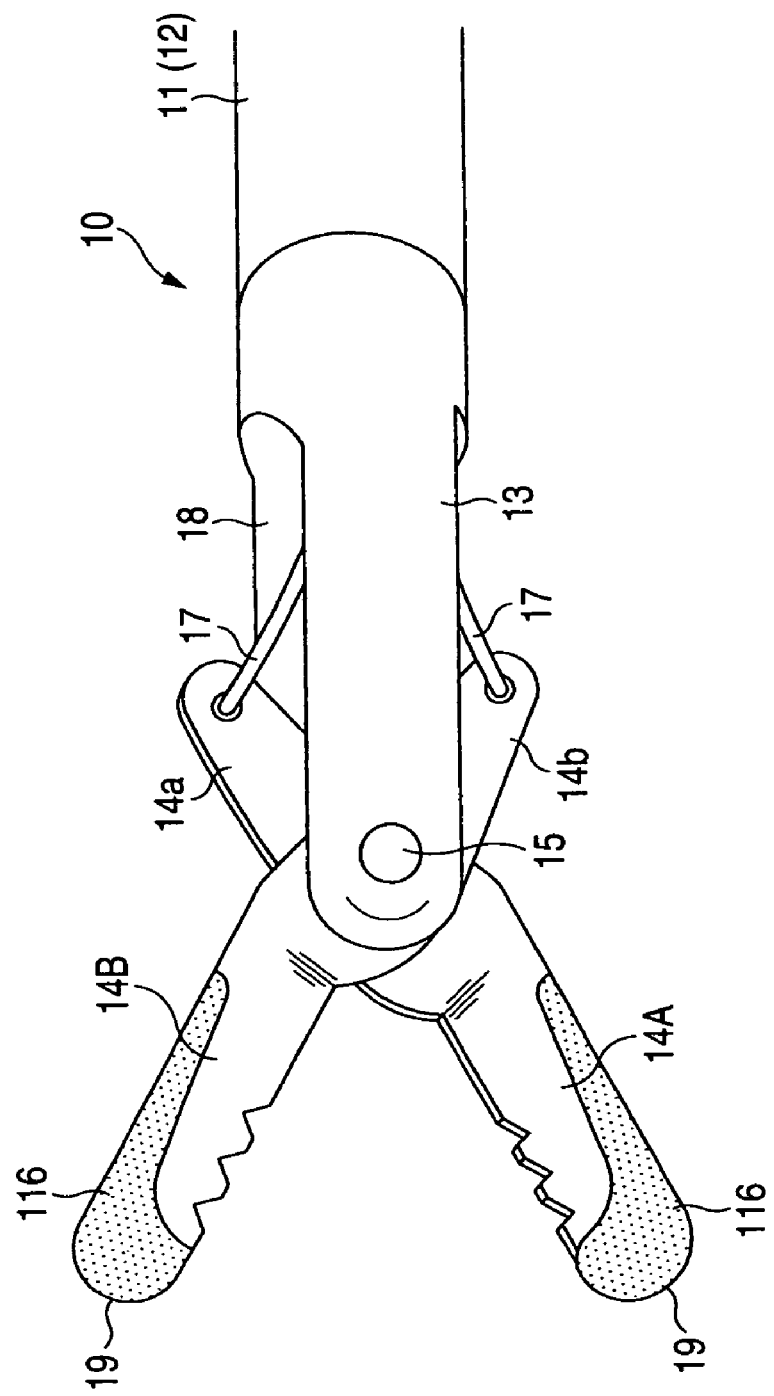
FIG. 12 is a perspective view of the high-frequency incision tool for endoscope according to the fifth embodiment of the invention when the electrode blades at the front end portion thereof are open.
Figure 13:
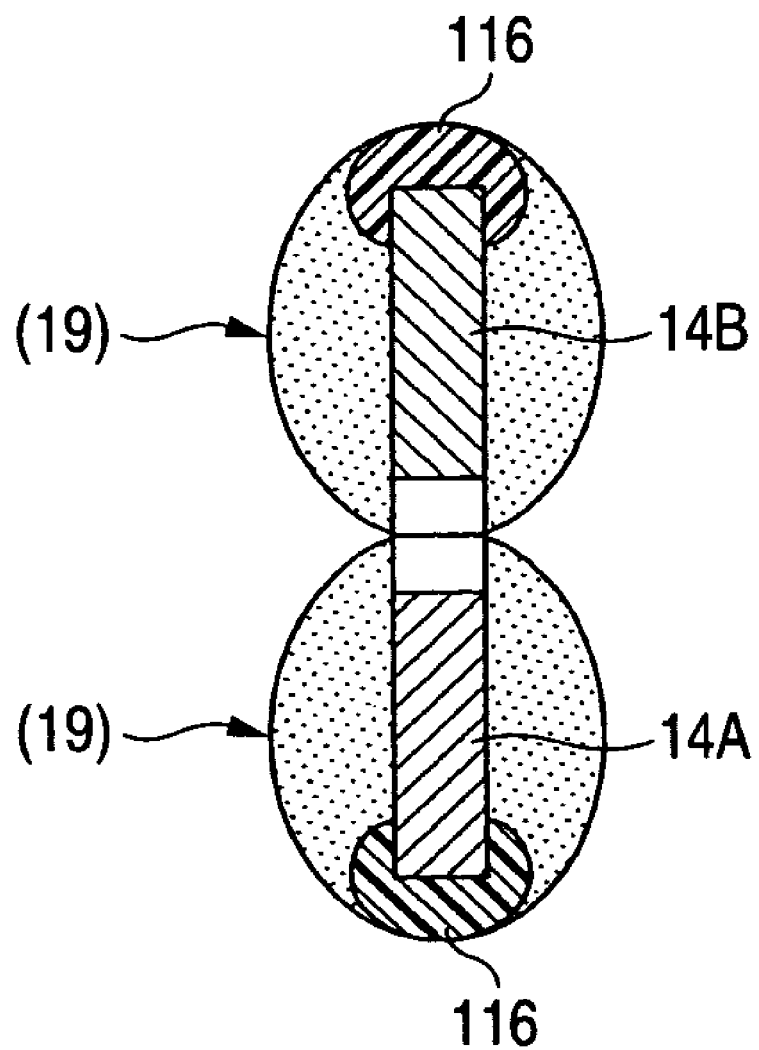
FIG. 13 is a cross-sectional view of the high-frequency incision tool for endoscope according to the fifth embodiment of the invention taken along the line B-B shown in FIG. 11.

FIGS. 11 to 13 show the high-frequency incision tool 10 according to a fifth embodiment of the invention. FIG. 11 is a side cross-sectional view when the electrode blades 14A and 14B are closed. FIG. 12 is a perspective view when the electrode blades 14A and 14B are open. FIG. 13 is a cross-sectional view taken along the line B-B shown in FIG. 11. Each of the electrode blades 14A and 14B of this embodiment, including its tip portion, is shaped into a thin plate as shown in FIG. 13, and a planar portion 19 is not formed at the tip portion itself of each of the electrode blades 14A and 14B. Instead, on the outer surface extending from the tip to the back side, when viewed in the opening/closing direction, of each of the electrode blades 14A and 14B is placed a heat-resistant, electrically insulating adhesive 116 (electrically insulating member), such as an epoxy- or silicon-based adhesive. The tip surface (the back side of the sand patterned part in FIG. 13) is chamfered into a smooth spherical shape, forming the planar portion 19.

Sixth Embodiment

Figure 14:
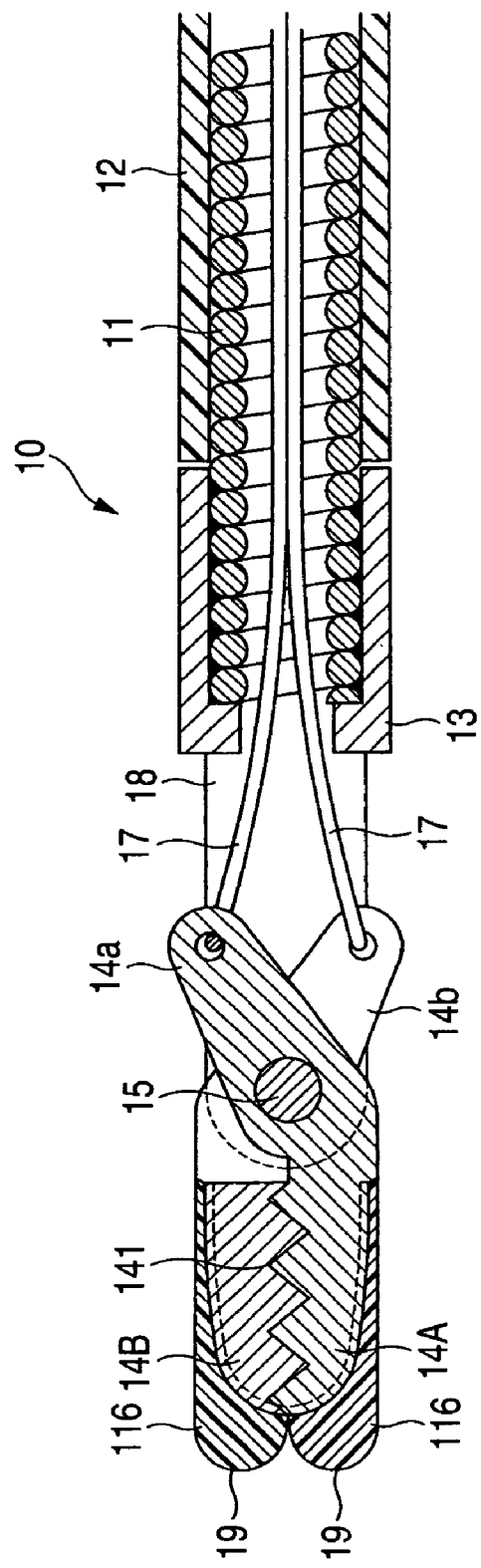
FIG. 14 is a cross-sectional side view of the high-frequency incision tool for endoscope according to the sixth embodiment of the invention when the electrode blades at the front end portion thereof are closed.
Figure 15:
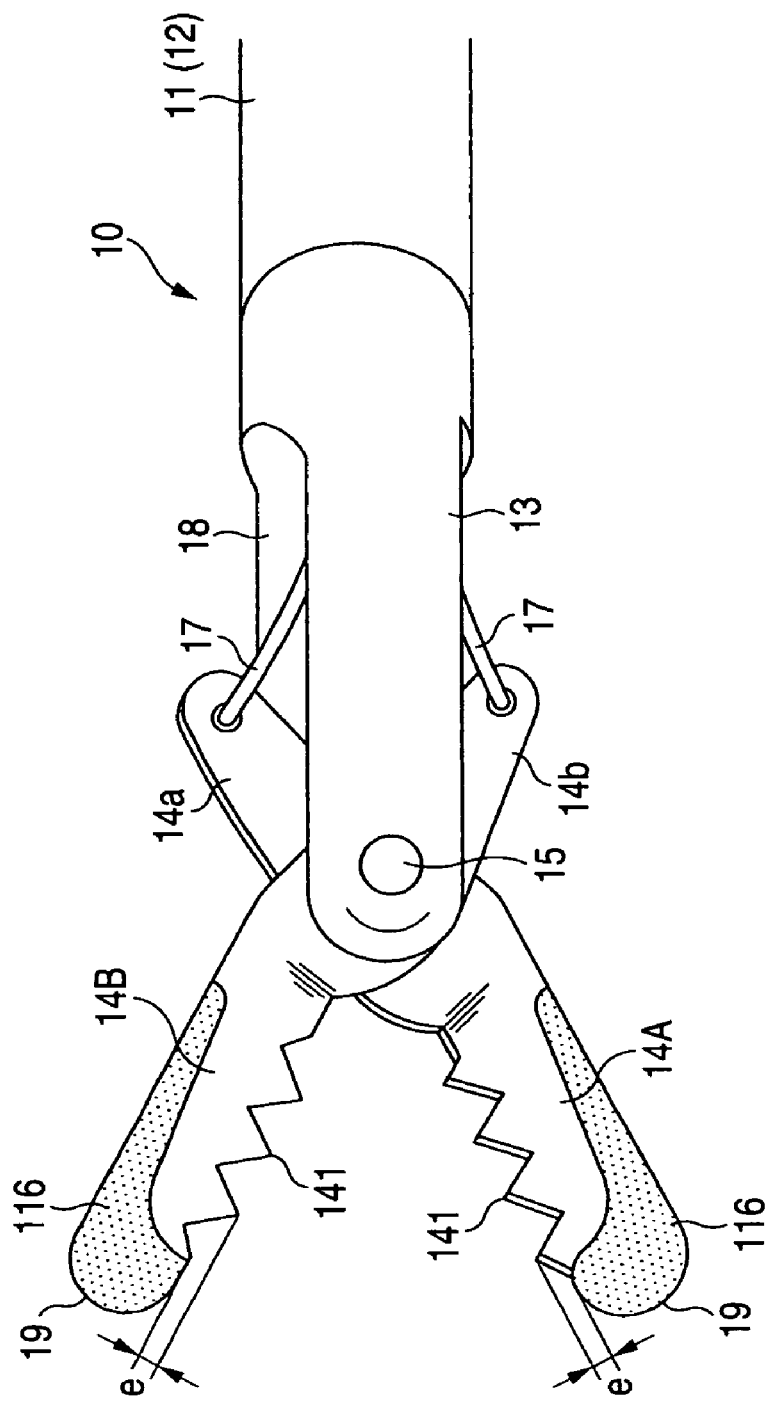
FIG. 15 is a perspective view of the high-frequency incision tool for endoscope according to the sixth embodiment of the invention when the electrode blades at the front end portion thereof are open.

FIGS. 14 and 15 show the high-frequency incision tool 10 according to a sixth embodiment of the invention. FIG. 14 is a side cross-sectional view when the electrode blades 14A and 14B are closed. FIG. 15 is a perspective view when the electrode blades 14A and 14B are open. In this embodiment, on the sides of the pair of the electrode blades 14A and 14B facing each other are formed successive projections and recesses, i.e., saw teeth 141 (hereinafter referred to as "saw tooth 141"). The apex of the saw tooth 141 projects toward the closing direction beyond the electrically insulating member 116 attached to each of the electrode blades 14A and 14B. That is, e>0 (desirably e≧0.2 mm) in FIG. 15. Therefore, high-frequency cauterization can be performed on the mucous membranes 6, muscle layers 7 or the like securely gripped with the saw teeth 141. Although the other portions are configured in the same manner as the fifth embodiment, this configuration may be applied to other embodiments.

Seventh Embodiment

Figure 16:
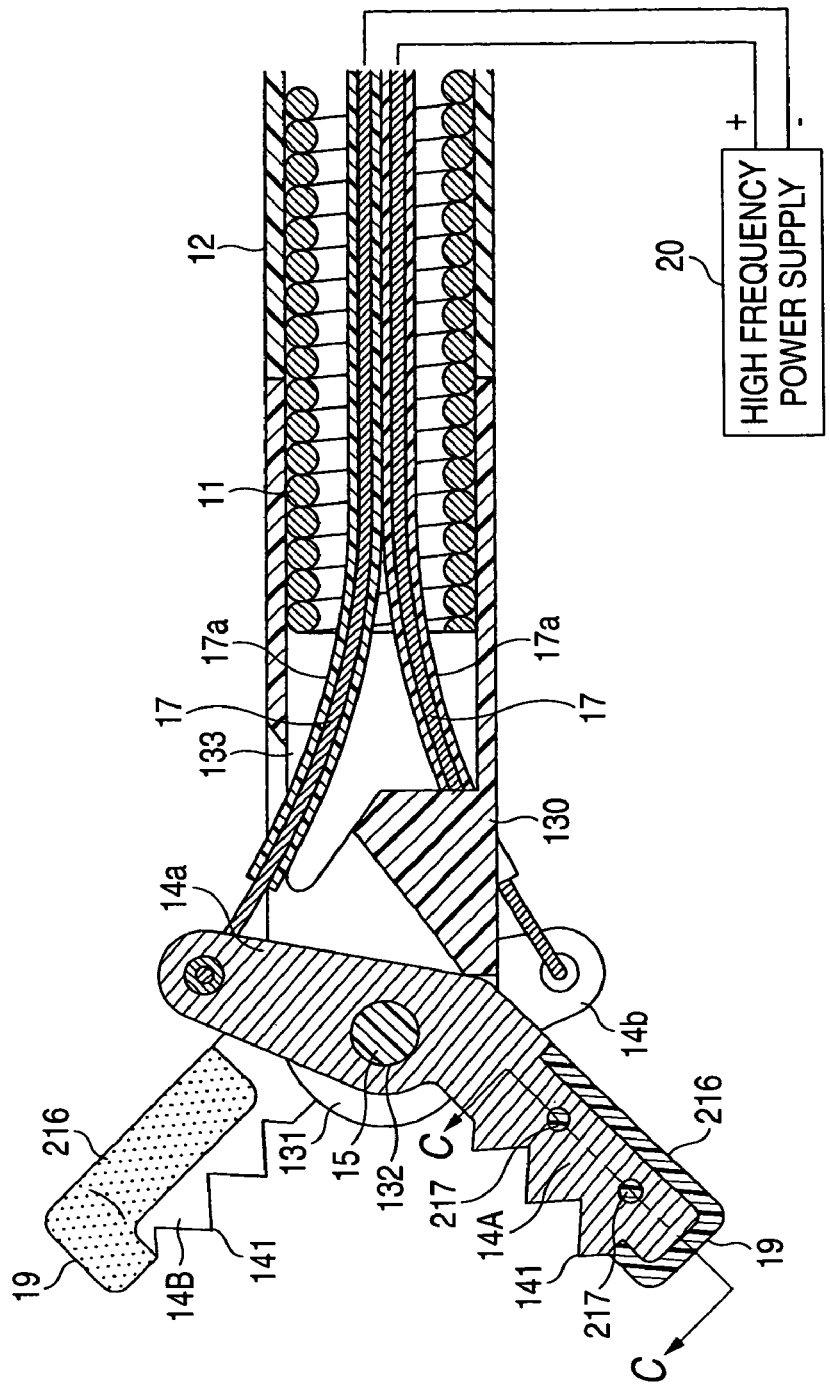
FIG. 16 is a cross-sectional side view of the high-frequency incision tool for endoscope according to the seventh embodiment of the invention when the electrode blades at the front end portion thereof are open
Figure 17:
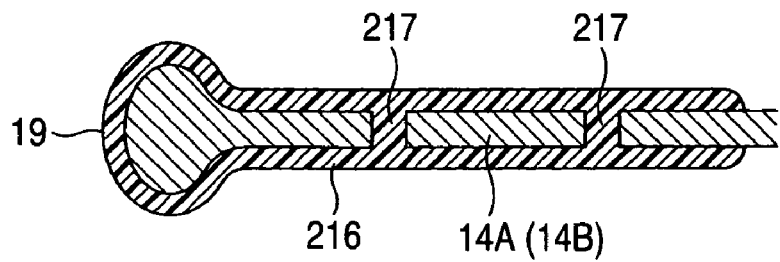
FIG. 17 is a cross-sectional view of the high-frequency incision tool for endoscope according to the seventh embodiment of the invention taken along the line C-C shown in FIG. 16.
Figure 18:
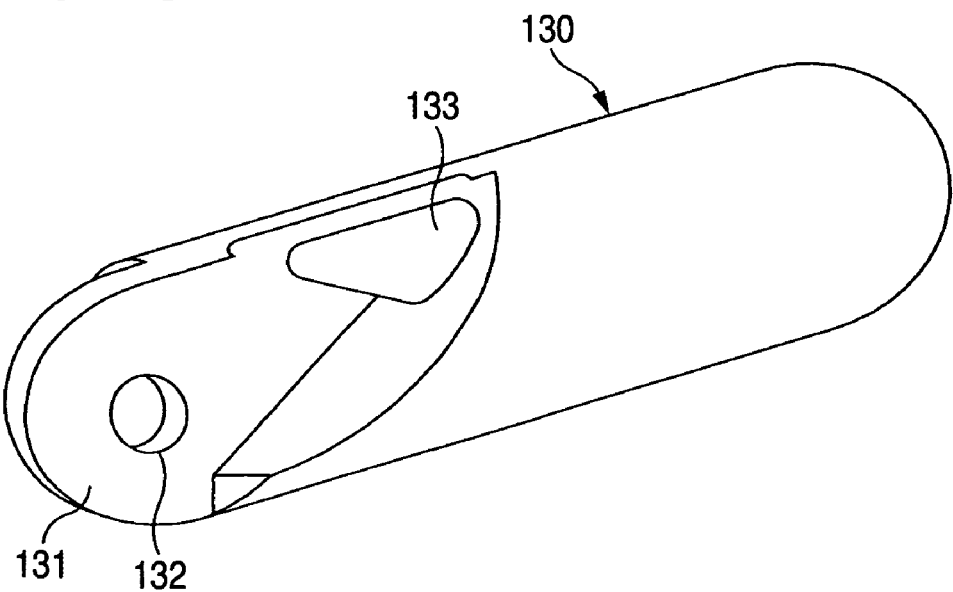
FIG. 18 is a perspective view showing only the front support member of the high-frequency incision tool for endoscope according to the seventh embodiment of the invention.

FIGS. 16 to 18 show the high-frequency incision tool 10 according to a seventh embodiment of the invention. FIG. 16 is a side cross-sectional view when the electrode blades 14A and 14B are open. FIG. 17 is a cross-sectional view taken along the line C-C shown in FIG. 16. FIG. 18 is a perspective view showing a front support member 130 alone. In this embodiment, an electrically insulating member 216 is attached to each of the electrode blades 14A and 14B such that the electrically insulating member 216 sandwiches each of the electrode blades 14A and 14B. The electrically insulating members 216 that sandwiches each of the electrode blades 14A and 14B connect to each other through a hole 217 drilled through each of the electrode blades 14A and 14B to form an integral part as shown in FIG. 17, resulting in a reinforced bonding F strength between the electrically insulating member 216 and each of the electrode blades 14A and 14B1 Each of the electrode blades 14A and 14B is formed such that its tip portion and therearound is molded or mechanically machined into a shape extending sideways, the surface of which is covered with the electrically insulating member 216 in a uniform thickness.

Furthermore, in this embodiment, the front support member 130 has, in the front center portion, a support tongue piece 131 for supporting the pair of electrode blades 14A and 14B, as shown alone in FIG. 18. The pair of electrode blades 14A and 14B are pivotably attached to the support tongue piece 131 such that it is sandwiched between the pair of electrode blades 14A and 14B. Reference number 132 denotes a support hole through which the rotation support shaft 15 is inserted, and reference number 133 denotes a wire passage hole through which the operation wire 17 is extracted.

Such front support member 130 and rotation support shaft 15 are both formed of an electrically insulating material. The pair of electrode blades 14A and 14B are arranged such that they do not electrically communicate with each other and connected to the positive and negative terminals of a high-frequency power supply 20, respectively, through a pair of conductive operation wires 17, each coated with an insulating coating 17*a*, forming a so-called bipolar high-frequency incision tool for endoscope. The invention may be applied to both monopolar and bipolar high-frequency incision tools.

The invention is not limited to the above embodiments as long as at least one of the pair of electrode blades 14A and 14B includes the planar portion 19. The mechanism for opening and closing the electrode blades 14A and 14B may be a known mechanism or the like in which the pair of electrode blades 14A and 14B is biased in the opening direction and opened and closed by advancing and retracting the electrode blades 14A and 14B out of or into the front end of the sheath 11 with the operation wire 17 inserted through the sheath 11, or conversely, by pushing and pulling the sheath 11.

What is claimed is:

1. A high-frequency incision tool for endoscope comprising:
    a sheath inserted through and extracted from a treatment tool guide lumen of an endoscope;
    an operation unit connected to a rear of the sheath;
    a pair of electrode blades disposed in parallel and oriented forward at a front position of the sheath, the pair of electrode blades being adapted to open and close through remote manipulation of the operation unit; and
    a planar portion provided at a tip of at least one of the electrode blades, the planar portion having a projected area, when viewed from the front, larger than a cross sectional area of the electrode blade at a portion close to a front end thereof,
    wherein the planar portion is formed of an electrically insulating member which is attached to the most distal tip of the electrode blade and encloses the most distal tip of the electrode blade and wraps around a portion of at least one adjacent side of the electrode blade.

2. The high-frequency incision tool according to claim 1, wherein the planar portion is formed so as to project sideways from the tip portion of the electrode blade.

3. The high-frequency incision tool according to claim 2, wherein the tip of the electrode blade is formed so as to bend sideways to form an L-shape.

4. The high-frequency incision tool according to claim 2, wherein each of the pair of electrode blades deviates sideways from extension of a center axis line of the front end portion of the sheath.

5. The high-frequency incision tool according to claim 2, wherein the tip of the electrode blade is formed in a T-shape with a crossbar of the T projecting sideways in opposite directions.

6. The high-frequency incision tool according to claim 1, wherein the electrically insulating member is attached to an outer surface of the electrode blade.

7. The high-frequency incision tool according to claim 6, wherein the electrically insulating member is an adhesive adhered to an area extending from the tip to a back side of the electrode blade, the back side representing a side viewed in the open/close direction of the blades.

8. The high-frequency incision tool according to claim 1, wherein the electrically insulating member is attached to the electrode blade, sandwiches the electrode blade and connects to the electrode blade through a hole drilled through the electrode blade to form an integral part.

9. The high-frequency incision tool according to claim 1, wherein saw teeth having successive projections and recesses are formed on opposite sides of the pair of electrode blades, and an apex of an individual saw tooth projects toward the closing direction beyond the electrically insulating member attached to the electrode blade.

10. The high-frequency incision tool according to claim 1, wherein the pair of electrode blades is biased in the opening direction and opened and closed by advancing and retracting the electrode blades out of or into the front end of the sheath with an operation wire inserted through the sheath.

11. The high-frequency incision tool according to claim 1, wherein the pair of the electrode blades is opened and closed around a shaft disposed in the front end portion of the sheath and an operation wire for driving the pair of the electrode blades is inserted through the sheath.

12. The high-frequency incision tool according to claim 11, wherein the operation wire is formed of a conductive member through which a high-frequency current is applied to the electrode blades.

13. The high-frequency incision tool according to claim 1, wherein each of the pair of the electrode blades is formed into a shape in which a cup of bawl-shaped biopsy forceps is cut in half.

14. The high-frequency incision tool according to claim 1, wherein a casing tube fits around the sheath throughout its length and the sheath and the electrode blades can freely rotate around an axis of the casing tube relative to the casing tube.

15. The high-frequency incision tool according to claim 14, wherein the operation unit can rotate the sheath and the electrode blades relative to the casing tube.

16. The high-frequency incision tool according to claim 14, wherein the sheath is formed of a close-wound metal coil and the casing tube is formed of an electrically insulating tube.

* * * * *